United States Patent [19]

Jordan et al.

[11] Patent Number: 5,331,408
[45] Date of Patent: Jul. 19, 1994

[54] ON-LINE MICRO FORMATION SENSOR

[75] Inventors: Byron D. Jordan, Pointe Claire; Nam G. Nguyen, Montreal; Peter E. Wrist, Baie D'Urfe, all of Canada

[73] Assignee: Pulp and Paper Research Institute of Canada, Pointe Claire, Canada

[21] Appl. No.: 940,902

[22] PCT Filed: May 28, 1990

[86] PCT No.: PCT/CA90/00172
§ 371 Date: Oct. 28, 1992
§ 102(e) Date: Oct. 28, 1992

[87] PCT Pub. No.: WO91/19186
PCT Pub. Date: Dec. 12, 1991

[51] Int. Cl.$^5$ .............................................. G01N 21/86
[52] U.S. Cl. ................................... 356/429; 250/559; 250/571
[58] Field of Search ................... 356/429, 430, 431; 250/559, 571

[56] References Cited

U.S. PATENT DOCUMENTS 3,196,072 7/1965 Wirtz .
4,019,819 4/1977 Lodzinski .
4,644,174 2/1987 Ouellette et al. .
4,648,712 3/1987 Brenholdt ............................ 356/429
5,092,678 3/1992 Chase et al. ......................... 356/429

FOREIGN PATENT DOCUMENTS 0329889 8/1989 European Pat. Off. .
3413558 10/1985 Fed. Rep. of Germany .

Primary Examiner—F. L. Evans
Attorney, Agent, or Firm—Swabey Ogilvy Renault

[57] ABSTRACT

An optical scanner includes a light source (39) which directs a beam of light at a web of moving paper whereby the beam of light is transmitted through the web of moving paper. The transmitted beam (43) is split by a beam splitter (19) to provide a first split beam (44) travelling in a machine direction and a second split beam (45) travelling in a cross-machine direction. The split beams are received by charge-coupled device linear arrays (15, 19) which provide analog signals having magnitudes proportional to the magnitude of light intensity of the split beams. The analog signals are fed to analog-to-digital converters which provide digital data at the output. The digital data is then used to compute paper formation descriptors including paper mass variation, floc size statistics and histogram, Fourier power spectra and paper anisotropy.

1 Claim, 3 Drawing Sheets

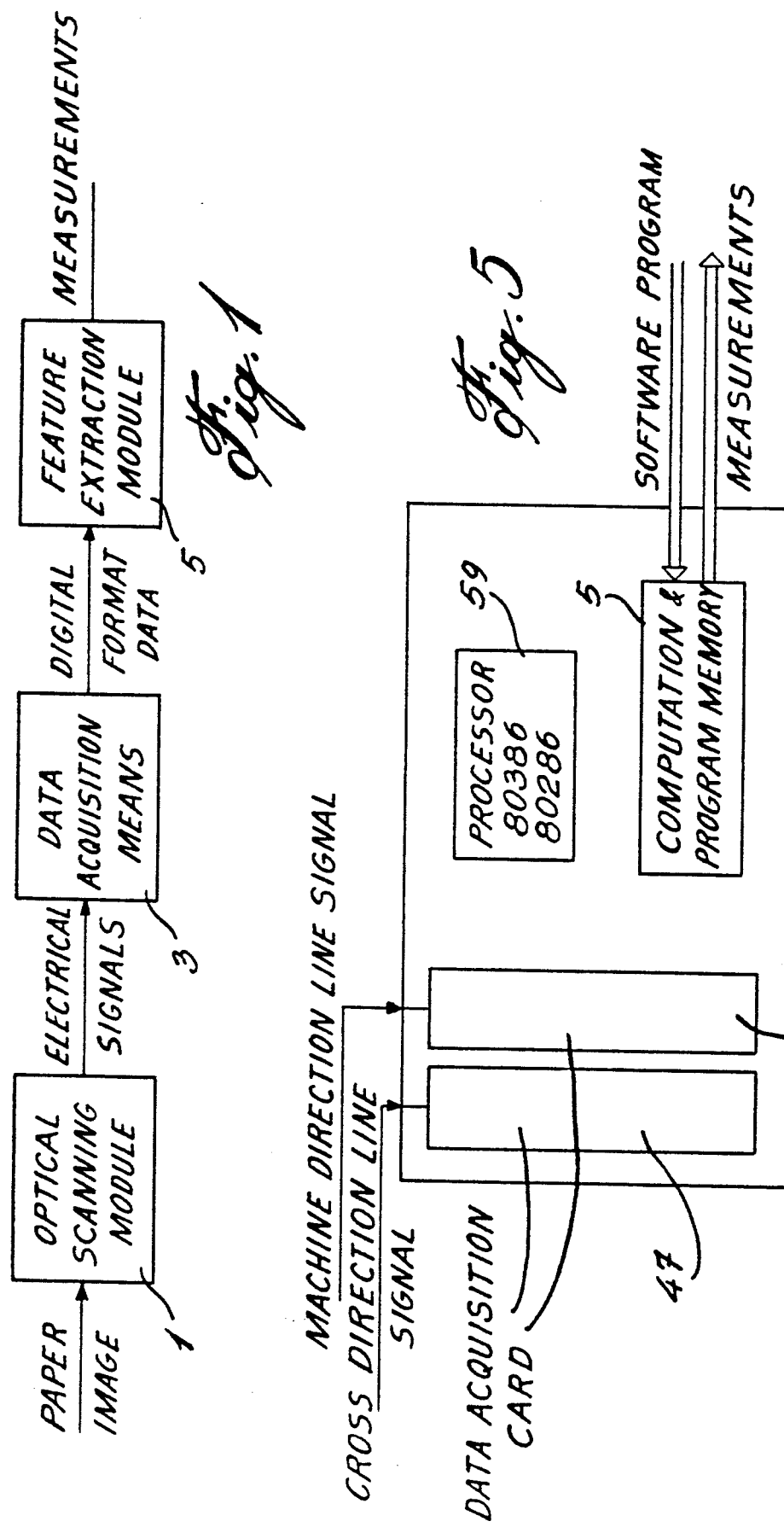

ON-LINE MICRO FORMATION SENSOR

TECHNICAL FIELD

The invention relates to an on-line paper micro formation sensor which measures and records paper formation descriptors. More specifically, the invention relates to such a sensor which measures and records paper formation descriptors including paper mass variation, floc size statistics and histrogram, Fourrier power spectra, and paper anisotropy.

BACKGROUND ART

Off-line paper formation sensors are known in the art. For example, the N.U.I. paper formation sensor, manufactured by NORAM Quality Control and Research Equipment Ltd. scans one spot at a time and can be used to measure paper mass variation. The Quebec North Shore Mead formation tester, manufactured by Electronic Associates, also scanned one spot at a time and gave wavelength power spectra. The Paprican Microscanner system, developed by the inventors herein and manufactured by NORAM Quality Control and Research Equipment Ltd., acquires a two-dimensional image and measures the mass variation, graininess as well as floc size histogram.

On-line paper formation sensors are also known in the art. Thus, the Measurex formation sensor, manufactured by Measurex, scans one spot at a time and gives mass variation measurements and floc size histogram. The Sentrol formation sensor also scans a single spot and extracts hard-clipped auto-correlation function as formation measurements. The Formspec formation analysis system, manufactured by Albany International, uses the visible light and a charge-coupled device (CCD) linear array. Because it looks at the whole width of the paper roll at a time, the whole paper formation variation along the width can be acquired quickly at the cost of low resolution.

The Intec system, manufactured by Intec Corp., also looks at the whole width of the paper roll at the same time but with a laser light source and a fiber optic receiver. It has the same advantages as well as disadvantages as the Formspec system. It is also designed to detect paper defects such as breaks, streaks and clustered or repeated holes. Accuray formation analysis system also scans the whole width of the paper roll at the same time along the cross direction using a linear array detector. It accumulates data of several scans, and an opacity variation coefficient, corresponding to each array element, is measured along the machine direction. Mass variation is obtained from the average of all of the opacity variation coefficients. The change in opacity variation coefficients along the cross direction gives some indications of cross direction uniformity. All of these on-line sensors are not capable of measuring paper anisotropy and of detecting pinholes accurately. Power spectra measurements, proven to be very useful with off-line systems, are also not addressed with any of the on-line systems.

Patents which contain teachings relating to paper formation sensors include U.S. Pat. No. 4,644,174, Ouellette et al, U.S. Pat. No. 4,019,819, Lodzinski and U.S. Pat. No. 3,196,072, Wirtz. The Ouellete et al patent teaches an application of analog filters to the spectral analysis of the transmitted profile of the formation. It neither uses detector arrays nor is it sensitive to machine direction/cross-machine direction variations. The Lodzinski patent teaches the measurement of optical properties, including opacity and Kubelka-Munk coefficients which are measured with on-line sensors in accordance with the teachings in this patent. However, formation measurement is not included in this patent.

The teachings in the Wirtz patent seem to be predicated on the idea that control of the space density of pulp fibers will allow control of the paper making process. A pressure replicate of the surface of the web is formed by pressing a plastic film against the surface with a roller and the plastic is then viewed in transillumination by an optical detector which counts the number of "fibers" per inch. This patent is of interest having regards to the present application in that it teaches the use of a reciprocating sensing head illustrated in FIG. 3 thereof. However, the sensing head does not have two separate linear arrays, nor does it have a beam splitter to split the light in the direction of both arrays. In addition, it does not obtain values for the same paper descriptors as the inventive system does.

DISCLOSURE OF THE INVENTION

It is therefore an object of the invention to provide an on-line paper micro formation sensor for measuring and recording paper formation descriptors of a web of moving paper.

It is a more specific object of the invention to provide such a sensor which includes a light source disposed to transmit light through the web of moving paper.

It is a still more specific object of the invention to provide such a counter wherein the transmitted light is split by a beam splitter, one of the split beams being directed to a machine direction sensor means and the other one of the split beams being directed to a cross-machine direction sensor means.

In accordance with the invention there is provided an on-line paper micro formation sensor for measuring and recording paper formation descriptors on a first surface of a web of moving paper, said web of moving paper also having a second surface, opposed to said first surface, said formation sensor comprising:

A) optical scanning means, comprising:

i) a light source spaced from said second surface of said web of moving paper for directing a beam of light at said second surface of said web of moving paper, said beam of light being transmitted through said web of moving paper;

ii) a beam splitter spaced from said first surface of said web of moving paper to receive said transmitted beam of light and to provide a first split beam, travelling in a first direction, and a second split beam, travelling in a second direction different from said first direction;

iii) machine direction sensor means, having an output terminal, placed to receive said first split beam and to provide a machine direction analog signal having a magnitude proportional to the magnitude of the light intensity of said first split beam;

iv) a cross-machine direction sensor, having an output terminal, placed to receive said second split beam and to provide a cross-machine direction analog signal having a magnitude proportional to the magnitude of the light intensity of said second split beam;

B) data acquisition means, comprising:

i) a machine direction module comprising a machine direction analog-to-digital converter having an input terminal and an output terminal, the input terminal of said machine direction analog-to-digital converter being connected to the output terminal of said machine direction sensor means, machine direction digital data being provided at said output terminal of said machine direction analog-to-digital converter, and machine direction digital storage means having an input terminal and an output terminal, the input terminal of said machine direction digital storage means being connected to the output terminal of said machine direction analog-to-digital converter;

ii) a cross-machine direction module comprising a cross-machine direction analog-to-digital converter having an input terminal and an output terminal, the input terminal of said cross-machine direction analog-to-digital converter being connected to the output terminal of said cross-machine direction sensor means, cross-machine direction digital data being provided at said output terminal of said cross-machine direction analog-to-digital converter, and cross-machine direction digital storage means having an input terminal and an output terminal, the input terminal of said cross-machine direction digital storage means being connected to the output terminal of said cross-machine direction analog-to-digital converter;

C) feature extraction means, comprising:

i) computation means having input terminals; said input terminals of said computation means being connected to the output terminals of both said machine direction and cross-machine direction digital storage means; whereby, to compute from both said machine direction and cross-machine direction digital data paper formation descriptors including paper mass variation, floc size statistics and histogram, Fourrier power spectra and paper anisotropy.

BRIEF DESCRIPTION OF DRAWINGS

The invention will be better understood by an examination of the following description, together with the accompanying drawings, in which:

FIG. 1 is schematic block diagram of the system;

FIG. 5 is a lay-out diagram of the data acquisition module and the feature extraction module.

DESCRIPTION OF PREFERRED EMBODIMENTS

Figure 2:
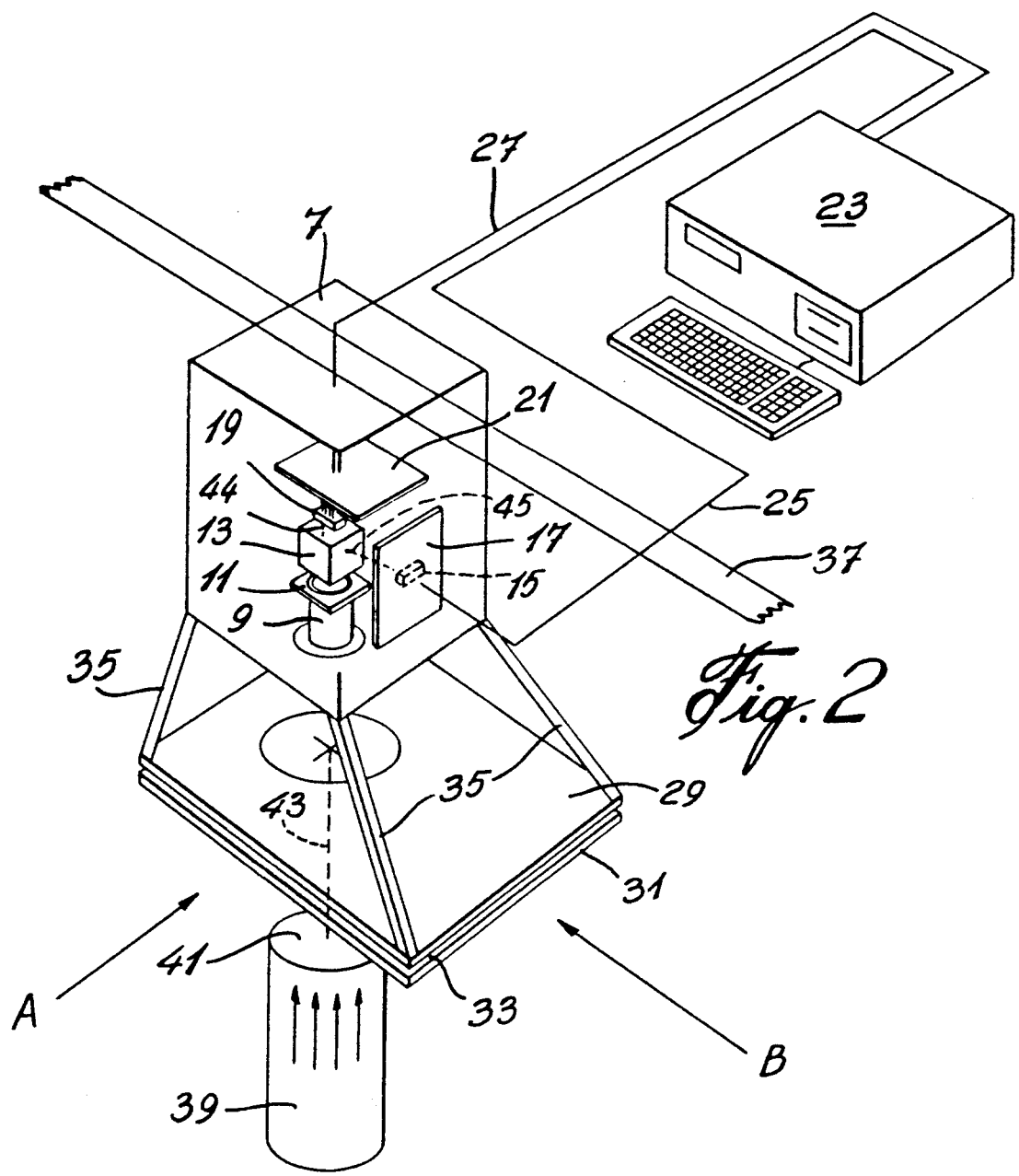
FIG. 2 is a perspective view of the optical scanning module.

The technology of two-dimensional array detectors, although sophisticated enough to give the required qualitative measurements, is still not fast enough for on-line paper formation measurements. Linear array detector technology, on the other hand, can operate almost at the speed limitation of the paper machine. Using two line array detectors, one viewing line along the cross-machine direction and the other along the machine direction, it becomes possible to derive most of the useful measurements. The micro formation sensor of the present application is devised using, in the preferred embodiment, this two line array detector concept.

The sensor of the present application is composed of three main components: an Optical Scanning module, followed by a data acquisition means and a Feature extraction module. Generally speaking, in the scanning module, transmitted light from a very high intensity light source is transmitted through a web of running paper. The transmitted light beam is split by a beam splitter onto two charge-coupled device line detectors, one above the beam splitter and the other on its side. Because the line detectors are oriented such that one records machine direction line image and the other records cross-machine direction line image, the device can be adjusted to look at a cross of selected size. For practical purposes, the size of 8 by 8 centimeters was chosen. Thus, any flocs ranging in size from 80 microns to 4 centimeters are accounted for.

In the data acquisition means, the two line images are digitized and then stored in dual port memories. In the Feature extraction module, digital data obtained from the dual port memories of the data acquisition means are processed to compensate for shading effect and to extract useful paper formation descriptors. These descriptors can be stored in memories or disks or printed on hard copies or displayed on monitors.

Turning now to FIG. 1, as can be seen, the system comprises an optical scanning module 1, a data acquisition means 3 and a Feature extraction module 5. Paper images, in the form of light beams, are transmitted to the optical scanning module where they are transformed to electrical analog signals. The electrical analog signals are fed to the data acquisition means where, amongst other things, they are transformed to digital data. In turn, the digital data is fed to the feature extraction module which performs computations to derive measurements such as paper mass variation, floc size statistics and histogram, Fourrier power spectra and paper anisotropy. In the preferred embodiment, the floc size ranges from 80 microns to 4 centimeters.

The output of the feature extraction module is fed to memories or disk or is printed on hard copies or can be displayed on monitors. The processes for converting the data to the paper formation descriptors are well known in the art. Thus, in an article entitled "Specific Perimeter - a graininess parameter for formation and print-mottle textures", Paperi ja Puu - Papper och Trä 6-7/1986, B. D. Jordan et al, pages 476 to 482, there is described an off-line method using a two-dimensional array image to extract the parameters:

CONTRAST: Describing the paper mass variation

SPECIFIC PERIMETER: Describing graininess in the paper or inverse of floc size in paper.

In another paper, entitled "Overview of texture analysis of print and paper", Paperi ja Puu-Paper and Timber 8/1989, N. G. Nguyen et al, there is described the Fourrier descriptors for an off-line image analyser using a two-dimensional array image. This same idea is applied to obtain Fourrier descriptors for the on-line sensor of the present application.

Referring now to FIG. 2, the optical scanning module comprises a housing 7. Disposed within the housing is a light guide 9 which guides light, as will be described below, to a focusing lens 11. After passing through the lens 11, the light beam is directed to a beam splitter 13 which directs one beam of light to a machine direction sensor means 15 which can comprise a camera, for example, a charge-coupled device (CCD) linear array sensor which is supported by a plate 17. The other split beam is directed at a cross-machine direction sensor 19, which comprises the same device as sensor 15, and which is supported from a plate 21. The outputs of sensors 15 and 19 are fed to a processor 23 via buses 25 and 27 respectively.

Spaced from the housing 7 (in the illustrated embodiment, underlying the housing 7) are paper guiding means comprising spaced stabilizer plates 29 and 31 having a space 33 between them. A web of paper to be tested moves in the machine direction, illustrated by the arrow A, in the space between the stabilizer plates. The guiding means is physically connected to the housing to move with the housing, as will be described below, by beams 35.

Figure 1A:
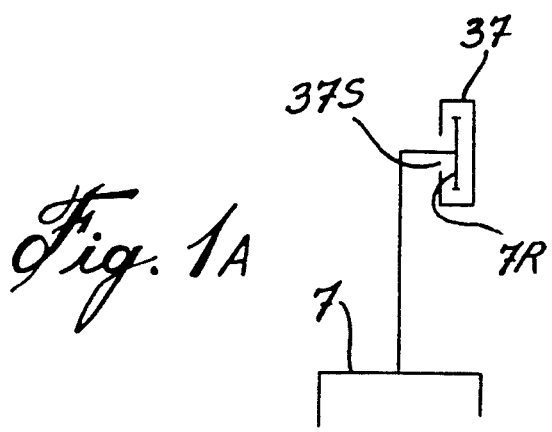
FIG. 1A illustrates a possible arrangement for driving the housing in cross-machine direction.

The housing 7 moves, reciprocally, in a cross-machine direction, illustrated by arrow B, along the rail 37 using means well known in the art. For example, as illustrated in FIG. 1A, housing 7 can be attached to a roller 7R which is guided for movement in the cross-machine direction by slot 37S in rail 37. The roller would be driven by a motor as is well known in the art.

A visible, high intensity light source 39, which is also movable with housing 7, is disposed to direct a beam of light 41 to one surface of the web of moving paper (in the illustrated embodiment, the bottom surface). The beam 41 is transmitted through the web of moving paper to provide a transmitted beam 43 which is received by the light guide 9. The light guide directs the beam 43 to the focusing lens 11 which in turn directs the focused beam to beam splitter 13.

Beam splitter 13 provides a first split beam 44, directed at the cross-machine direction sensor 19, and a second split beam 45, directed at the machine direction sensor 15.

Figure 3:
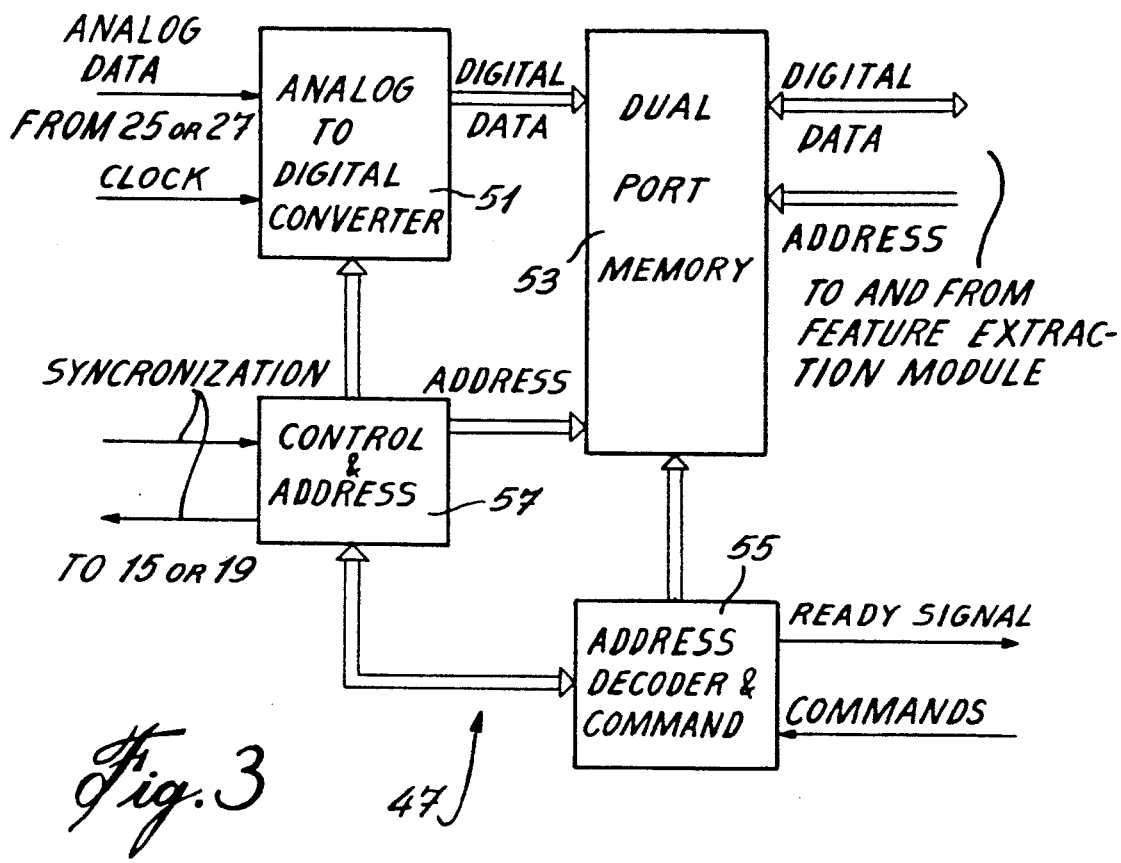
FIG. 3 is a schematic diagram of a data acquisition module.

The outputs of sensors 15 and 19 are transmitted to the data acquisition means which is mounted in the processor 23 and comprises a cross-machine direction data acquisition card 47, and a machine direction data acquisition card 49 illustrated in FIG. 5. Mounted on each card is a data acquisition module, and the data acquisition modules of both cards are identical and illustrated in FIG. 3. The data acquisition modules comprise an analog-to-digital converter 51 which has an input terminal to which is connected bus 25 or 27. An output terminal of the analog-to-digital converter 51 is connected to an input terminal of a storage means, for example, dual port memory 53.

An address decoder 55 has an output terminal which is connected to a control terminal of the dual port memory 53 and it further includes an input/output terminal which is connected to an input/output terminal of control and address arrangement 57. The address decoder and command arrangement 55 also has an input terminal for receiving commands from the feature extraction module as will be explained below, and an output terminal for providing a ready signal to the feature extraction module as will also be explained below.

The control and address arrangement 57 also has an input terminal for receiving a synchronization signal and an output terminal connected to a control terminal of the sensor means 15 or 19.

Figure 4:
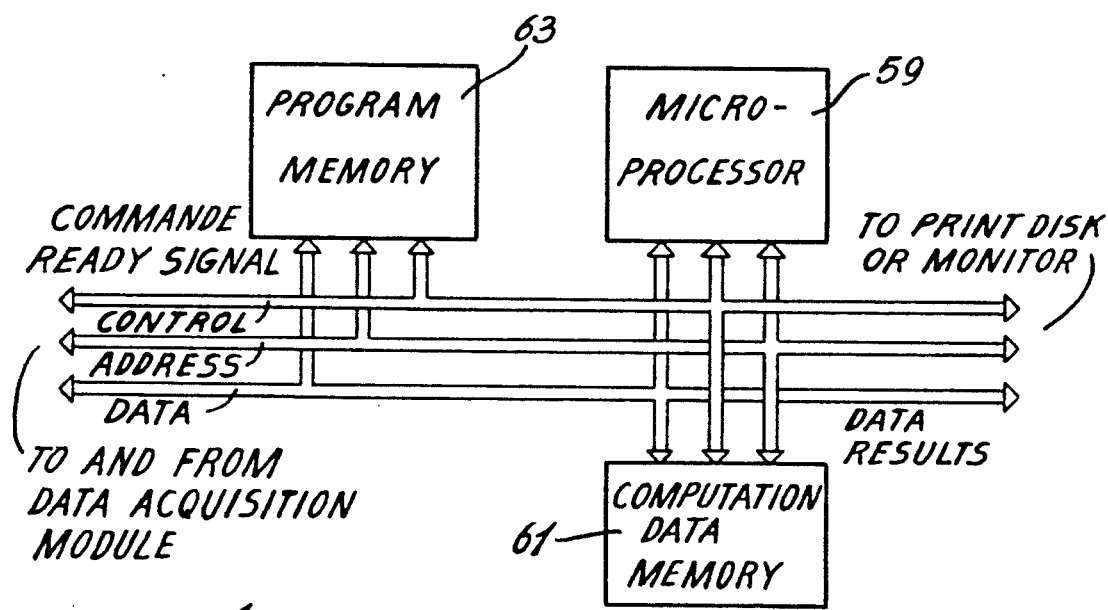
FIG. 4 is a schematic diagram of the feature extraction module.

Turning now to FIG. 4, the feature extraction module includes a processing element 59 of the processor 23 as well as a computation data memory 61. The program for driving the process is stored in program memory 63.

In operation, the sensor works as follows:

The process is initiated by the feature extraction module which will transmit a data acquisition command under control of software at predetermined intervals. The data acquisition command is transmitted to the data acquisition modules and, upon receiving this command, the data acquisition modules relay signals to sensors 15 and 19 of the optical scanning module. Upon receipt of these signals, the line signals of the sensors are frozen and remain frozen during the entire data acquisition period. The analog signals of the sensors are transmitted to the analog-to-digital converter 51 of their respective data acquisition modules where they are converted into digital format at a high speed by the 20 megahertz analog-to-digital converter 51. The digital signals are then stored in the dual port memory 53 of the respective data acquisition modules, and, when the storage of each entire linear array is completed, a ready signal is sent by arrangements 55 of the data acquisition modules to the feature extraction module indicating that the dual port memories 53 are ready for processing. Upon receiving the ready signal from the data acquisition modules, the feature extraction module retrieves data from the dual port memories 51 of the data acquisition modules and performs necessary computation for shading correction and for deriving values for the paper formation descriptors as above enumerated. Such computational methods are well known in the art but generally, in accordance with the invention, have the following features:

CONTRAST: is measured on the cross direction sensor as mass variation.

MEAN RUNLENGTH at 50% detection: ms measured on the cross direction sensor as the floc size measurement.

RATIO OF MEAN RUNLENGTH: the ratio of machine direction runlength to cross-machine direction run-length is used as a measure of anisotropy. Since the sensors move along the cross-machine direction, the profile along the whole width of the paper roll can be recorded.

The Fourrier power spectra can be measured using the ideas in the paper entitled "Overview of texture analysis of print and paper" referred to above. Although this paper deals with Fourrier descriptors for an off-line image analyser using a two-dimensional image, the same ideas can be applied to obtain one-dimensional Fourrier descriptors for the on-line sensor.

The computed values for the descriptors can then be sent to either a printer, a disk or a monitor.

In a developed embodiment, the data acquisition modules, as above-discussed, are designed as two identical but separate cards which can be inserted into two slots of a personal computer such as an IBM PC. The cards are considered by the IBM PC as its memory cards. The feature extraction module is the combination of the IBM PC and the software programs to synchronize events, compute measurements, store, print out or display results. The software procedure for a complete measurement on one linear array scan is as follows:

STEP 1: Acquire a line image
STEP 2: Wait till STEP1 is done
STEP 3: Compute measurements from acquired image
STEP 4. Accumulate data and present results.

When doing measurements for two linear array images, of both machine direction and cross-machine direction, waiting time for data acquisitions can be saved. The principle is to compute the measurements of the cross-machine direction image while waiting for the completion of the data acquisition of the machine direction image and vice-versa. The program STEPS would be as follows:

STEP 1: acquire a cross direction image
STEP 2: Wait till STEP 1 is done
STEP 3: Acquire a machine direction image STEP 4: Compute measurements of acquired cross direction image STEP 5: Accumulate cross direction data STEP 6: Acquire a cross direction image STEP 7: Compute measurements of acquired machine direction image STEP 8: Accumulate machine direction data STEP 9: Compute and accumulate machine to cross direction ratios STEP 10: Present results STEP 11: If finished control signa not received, go to STEP 3 for more measurements. Otherwise, go to STEP 12

STEP 12: Stop

Note that STEP1 and STEP2 are required because one line image has to be stored initially before any measurements can be calculated. The waiting time for machine direction acquisition after STEP3 is compensated for by the time required for processing stored cross-machine direction images in STEP4 and STEP5. Conversely, the waiting time for cross-machine direction acquisition after STEP6 is compensated for by the time required for processing the stored machine direction image in STEP7 and STEP8.

It is also noted that, if reflected light is used instead of transmitted light in the optical scanning unit, the sensor can become a tool for evaluating paper gloss and print non-uniformity on-line.

Although a particular embodiment has been described, this was for the purpose of illustrating, but not limiting, the invention. Various modifications, which will come readily to the mind of one skilled in the art, are within the scope of the invention as defined in the appended claims.

We claim:

1. An on-line paper micro formation sensor for measuring and recording paper formation descriptors on a first surface of a web of moving paper, said web of moving paper also having a second surface, opposed to said first surface, said formation sensor comprising:

A) optical scanning means, comprising:
   i) a light source spaced from said second surface of said web of moving paper for directing a beam of light at said second surface of said web of moving paper, said beam of light being transmitted through said web of moving paper;
   ii) a beam splitter spaced from said first surface of said web of moving paper to receive said transmitted beam of light and to provide a first split beam, travelling in a first direction, and a second split beam, travelling in a second direction different form said first direction;
   iii) machine direction sensor means, having an output terminal, placed to receive said first split beam and to provide a machine direction analog signal having a magnitude proportional to the magnitude of the light intensity of said first split beam;
   iv) a cross-machine direction sensor means, having an output terminal, placed to receive said second split beam and to provide a cross-machine direction analog signal having a magnitude proportional to the magnitude of the light intensity of said second split beam;

B) data acquisition means, comprising:
   i) a machine direction module comprising a machine direction analog-to-digital converter having an input terminal and an output terminal, the input terminal of said machine direction analog-to-digital converter being connected to the output terminal of said machine direction sensor means, machine direction digital data being provided at said output terminal of said machine direction analog-to-digital converter, and machine direction digital storage means having an input terminal and an output terminal, the input terminal of said machine direction digital storage means being connected to the output terminal of said machine direction analog-to-digital converter;
   ii) a cross-machine direction module comprising a cross-machine direction analog-to-digital converter having an input terminal and an output terminal, the input terminal of said cross-machine direction analog-to-digital converter being connected to the output terminal of said cross-machine direction sensor means, cross-machine direction digital data being provided at said output terminal of said cross-machine direction analog-to-digital converter, said cross-machine direction digital storage means having an input terminal and an output terminal, the input terminal of said cross-machine direction digital storage means being connected to the output terminal of said cross-machine direction analog-to-digital converter;

C) feature extraction means, comprising:
   i) computation means having input terminals; said input terminals of said computation means being connected to the output terminals of both said machine direction and cross-machine direction digital storage means;

whereby, to compute from both said machine direction and cross-machine direction digital data paper formation descriptors including paper mass variation, floc size statistics and histogram, Fourrier power spectra and paper anisotropy;

said beam splitter, said machine direction sensor means and said cross-machine direction sensor means are mounted in a housing, said housing being reciprocally movable in a cross-machine direction;

and further including a light guide disposed between said light source and said beam splitter in said housing;

said light source being movable with said housing;

and wherein both said machine direction sensor means and said cross-machine direction sensor means comprise charge coupled device linear arrays.

* * * * *